United States Patent [19]

MacCoss et al.

[11] Patent Number: 4,670,424

[45] Date of Patent: Jun. 2, 1987

[54] CYCLIC PYROPHOSPHATES OF PURINE AND PYRIMIDINE ACYCLONUCLEOSIDES

[75] Inventors: Malcolm MacCoss, Freehold; Richard Tolman, Warren, both of N.J.

[73] Assignee: Merck & Co., Inc., Rahway, N.J.

[21] Appl. No.: 533,676

[22] Filed: Sep. 19, 1983

[51] Int. Cl.$^4$ .................. A61K 31/52; A61K 31/505; C07D 473/18; C07D 473/34; C07D 239/55

[52] U.S. Cl. ........................................ 514/81; 514/86; 544/243; 544/244

[58] Field of Search ............... 544/243, 244; 514/81, 514/86

[56] References Cited

U.S. PATENT DOCUMENTS 4,287,188  9/1981  Schaeffer ................. 544/244 X
4,347,360  8/1982  Ogilvie ..................... 544/276

FOREIGN PATENT DOCUMENTS 0074306  8/1982  European Pat. Off. .
  31069  7/1972  Japan ....................... 544/244

OTHER PUBLICATIONS

Gauri, et al., Chem. Abstracts, vol. 94 (1981), entry 58495x.
Gauri, et al., Chem. Abstracts, vol. 94 (1981), entry 84455d.
Burger, ed., *Medicinal Chemistry*, 3rd Edition Part I, Wiley–Interscience, (1970), pp. 662–663.
Jong-Ching Su and W. Z. Hassid–Carbohydrates and Nucleotides in Red Alga Porphyra Perforata; Biochemistry–pp. 474–480; vol. 1, No. 3, May 1962.
David Lipkin, Roy Markham & William H. Cook The Degradation of Adenosine-5'-Triphosphoric Acid (ATP) by Means of Aqueous Barium Hydroxide–Nov. 20, 1959–pp. 6075–6081.

*Primary Examiner*—Donald G. Daus
*Assistant Examiner*—William A. Teoli, Jr.
*Attorney, Agent, or Firm*—Richard A. Elder; Hesna J. Pfeiffer

[57] ABSTRACT

A compound of the formula R—CH$_2$—O—W and its pharmaceutically acceptable salts wherein R is a purine, a substituted purine, a pyrimidine or a substituted pyrimidine, wherein the substituents on the purine or pyrimidine are selected from amino, hydroxyl, halogen, thiol or alkylthio wherein the alkyl moiety of the alkylthiol has 1 to 6 carbon atoms; and W is

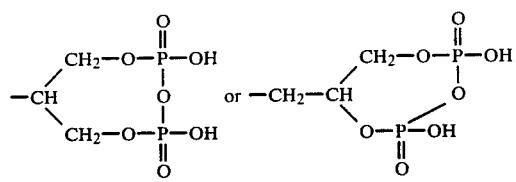

The compounds have antiviral activity.

14 Claims, No Drawings

CYCLIC PYROPHOSPHATES OF PURINE AND PYRIMIDINE ACYCLONUCLEOSIDES

The present invention relates to cyclic pyrophosphates of purine and pyrimidine acyclonucleosides. These compounds have antiviral activity. The compounds are particularly effective against herpes viruses, e.g. herpes simplex virus. The present invention also relates to methods of preparing cyclic phosphates of purine and pyrimidine acyclonucleosides.

The compounds of the invention are compounds of the formula R—$CH_2$—O—W and the pharmaceutically acceptable salts thereof wherein R is a substituted purine or a substituted pyrimidine, wherein the substituents on the purine or pyrimidine are selected from amino, hydroxyl, halogen (i.e. fluoro, chloro, bromo and iodo), thiol, or alkylthiol wherein the alkyl moiety of the alkylthiol has 1 to 6 carbon atoms; and W is

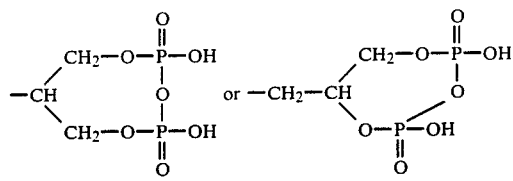

Examples of R are guanine, adenine, 2,6-diaminopurine, cytosine, thymine, uracil and 5-fluorouracil. R is preferably guanine, adenine or 2,6-diaminopurine. Guanine is especially preferred.

When W has the preceding two structures, the compounds of the invention are represented as follows:

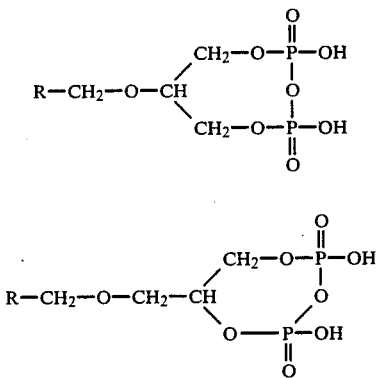

wherein R is as defined above.

Compounds wherein W comprises a seven-membered ring (a cyclic pyrophosphate of a substituted vicinal diol) contain an asymmetric carbon atom and can exist as R and S enantiomers.

When R is a guanine that is attached at its 9-position the resulting compounds of the present invention are represented as follows:

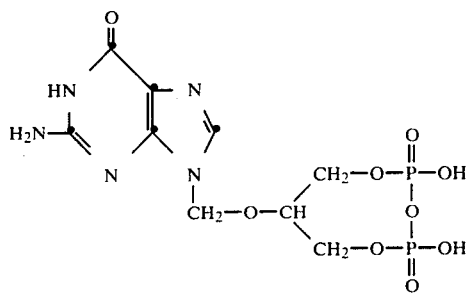

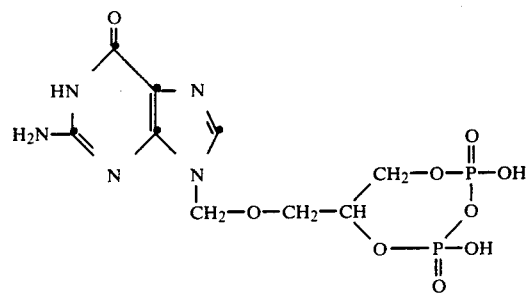

The present invention also relates to bis-monophosphates having the formula $R^1$—$CH_2$—O—Z wherein $R^1$ is a substituted purine or a substituted pyrimidine, wherein the substituents on the purine or pyrimidine are selected from amino, hydroxyl, halogen (i.e., fluoro, chloro, bromo and iodo), thiol or alkylthiol wherein the alkyl moiety of the alkylthiol has 1 to 6 carbon atoms, and Z is

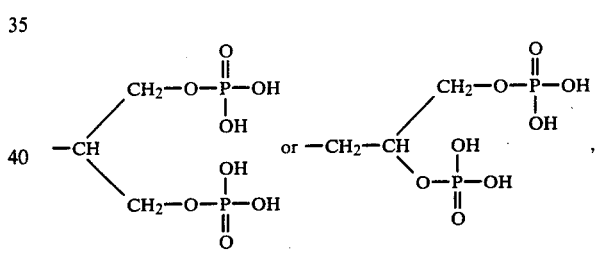

with the proviso that $R^1$ cannot be guanine. Examples of $R^1$ are adenine, 2,6-diaminopurine, cytosine, thymine, uracil and 5-fluorouracil. These bis-monophosphates are useful intermediates in preparing the cyclic pyrophosphates of the present invention.

While the purines and pyrimidines that are represented by R and $R^1$, as defined above, may be attached to the $CH_2$—O—W or $CH_2$—O—Z moieties from various positions on purines and pyrimidines, the preferred position for the purines is the 9-position and the preferred position for the pyrimidines is the 1-position.

The following are representative compounds of the present invention:
9-[(1,3-dihydroxy-2-propoxy)methyl]guanine cyclic pyrophosphate;
9-[(2,3-dihydroxy-1-propoxy)methyl]guanine cyclic pyrophosphate;
9-[(1,3-dihydroxy-2-propoxy)methyl]adenine cyclic pyrophosphate;
9-[(2,3-dihydroxy-1-propoxy)methyl]adenine cyclic pyrophosphate;
1-[(1,3-dihydroxy-2-propoxy)methyl]uracil cyclic pyrophosphate;

1-[(2,3-dihydroxy-1-propoxy)methyl]uracil cyclic pyrophosphate;
1-[(1,3-dihydroxy-2-propoxy)methyl]-5-fluorouracil cyclic pyrophosphate;
1-[(2,3-dihydroxy-1-propoxy)methyl]-5-fluorouracil cyclic pyrophosphate;
1-[(1,3-dihydroxy-2-propoxy)methyl]thymine cyclic pyrophosphate;
1-[(2,3-dihydroxy-1-propoxy)methyl]thymine cyclic pyrophosphate;
9-[(1,3-dihydroxy-2-propoxy)methyl]-2,6-diaminopurine cyclic pyrophosphate;
9-[(2,3-dihydroxy-1-propoxy)methyl]-2,6-diaminopurine cyclic pyrophosphate;
9-[(1,3-dihydroxy-2-propoxy)methyl]-2-aminopurine-6-thione cyclic pyrophosphate;
9-[(2,3-dihydroxy-1-propoxy)methyl]-2-aminopurine-6-thione cyclic pyrophosphate;
9-[(1,3-dihydroxy-2-propoxy)methyl-2-amino-6-chloropurine cyclic pyrophosphate;
9-[(2,3-dihydroxy-1-propoxy)methyl-2-amino-6-chloropurine cyclic pyrophosphate;
9-[(1,3-dihydroxy-2-propoxy)methyl-2-amino-6-methylmercaptopurine cyclic pyrophosphate;
9-[(2,3-dihydroxy-1-propoxy)methyl-2-amino-6-methylmercaptopurine cyclic pyrophosphate.

The following are preferred compounds of the present invention:

9-[1,3-dihydroxy-2-propoxy)methyl]guanine cyclic pyrophosphate; and
9-[2,3-dihydroxy-1-propoxy)methyl]guanine cyclic pyrophosphate.

Alternatively, the two preferred compounds, for example, can be named as follows:

9-[(2,4-dihydroxy-1,3,5,2,4-trioxadiphosphocan-7-yl)oxymethyl)guanine P,P'-dioxide]; and
9-[(2,4-dihydroxy-1,3,5,2,4-trioxadiphosphepan-6-yl)methoxymethyl)guanine P,P'-dioxide].

Acyclonucleoside cyclic pyrophosphates are prepared by treating the appropriately substituted and protected or unprotected purine or pyrimidine acyclonucleoside with an excess of a phosphorylating agent such as phosphorus oxychloride in an inert solvent such as triethylphosphate. The resulting bis-monophosphate is isolated, usually by ion exchange chromatography on an anion exchange resin such as Dowex 1×2, formate form. In the case where the acyclonucleoside contains a secondary hydroxyl, these conditions give the cyclic monophosphate as the major product. Thus, bis-monophosphates derived from a compound containing a secondary hydroxyl are preferentially prepared using an excess of a suitably protected monofunctional phosphorylating agent, such as dibenzylphosphorochloridate or bis(2,2,2-trichloroethyl)phosphorochloridate in an aprotic solvent such as triethyl phosphate or pyridine and deprotecting by standard methods. Cyclization of the bis-monophosphate is accomplished with an excess of a carbodiimide such as dicyclohexyl carbodiimide in a suitable solvent such as aqueous pyridine to afford the cyclic pyrophosphate product.

Pharmaceutically acceptable salts of cyclic pyrophosphates are conveniently prepared from the corresponding free acids by titration with an appropriate base, or by the use of an appropriate cation exchange resin, followed by lyophilization and/or crystallization. Acceptable cations include alkali metals, alkaline earth metals, ammonium, and substituted ammonium (wherein the substituent is alkyl having 1 to 8 carbon atoms). Preferred cations are sodium, potassium, ammonium and tributylammonium.

Halopurines which are used as starting materials in the preparation of compounds of the present invention are known in the literature. Halopurine acyclonucleosides are prepared by methods disclosed in European Patent Application 82401571.3, Publication No. 0 074 306, published Mar. 16, 1983; K. K. Ogilvie and M. F. Gillen, *Tetrahedron Letters*, Vol. 21, 327–330 (1980); and H. J. Shaeffer et al., *Nature*, Vol. 272, 583–585 (1978). The appropriate halopurine acyclonucleosides can be used directly to make the cyclic pyrophosphates. These cyclic pyrophosphates can also be treated with an alkylthiol in the presence of strong base to yield the corresponding alkylthiol purine derivatives.

Pyrimidine acyclonucleosides with the desired ring substitution are synthesized by literature methods such as disclosed in European Patent Application 81106460.9, Publication No. 0 046 307, published Feb. 24, 1982; H. M. Abrams et al., *J. Heterocyclic Chem.*, 18, 947–951 (1981); and K. K. Ogilvie and M. F. Gillen, *Tetrahedron Letters*, Vol. 21, 327–330 (1980). The pyrimidine acyclonucleosides are phosphorylated by methods disclosed herein and ring closed to yield cyclic pyrophosphates.

In another aspect of the invention there is provided a pharmaceutical composition or preparation comprising a compound of the formula R—CH$_2$—O—W wherein W and R are hereinbefore defined; or a pharmaceutically acceptable salt thereof; together with a pharmaceutically acceptable carrier therefor. In particular aspect the pharmaceutical composition comprises a compound of the formula R—CH$_2$—O—W wherein W and R are hereinbefore defined in effective unit dosage form.

As used herein the term "effective unit dosage" or "effective unit dose" is denoted to mean a predetermined antiviral amount sufficient to be effective against the viral organisms in vivo. Pharmaceutically acceptable carriers are materials useful for the purpose of administering the medicament, and may be solid, liquid or gaseous materials, which are otherwise inert and medically acceptable and are compatible with the active ingredients.

These pharmaceutical compositions may be given parenterally, orally, used as a suppository or pessary, applied topically as an ointment, cream, aerosol, powder, or given as eye or nose drops, etc., depending on whether the preparation is used to treat internal or external viral infections.

For internal infections the compositions are administered orally or parenterally at dose levels, calculated as the free base, of about 0.1 to 250 mg per kg, preferably 1.0 to 50 mg per kg of mammal body weight, and are used in man in a unit dosage form, administered, e.g. a few times daily, in the amount of 1 to 250 mg per unit dose.

For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavoring, preserving, suspending, thickening or emulsifying agents may be included. Tablets and granules are preferred, and these may be coated.

For parenteral administration or for administration as drops, as for eye infections, the compounds may be presented in aqueous solution in a concentration of from about 0.1 to 10% more preferably 0.1 to 7%, most preferably 0.2% w/v. The solution may contain antioxidants, buffers, etc.

Alternatively for infections of the eye, or other external tissues, e.g. mouth and skin, the compositions are preferably applied to the infected part of the body of the patient as a topical ointment or cream. The compounds may be presented in an ointment, for instance, with a water soluble ointment base, or in a cream, for instance with an oil in water cream base, in a concentration of from about 0.1 to 10%, preferably 0.1 to 7%, most preferably 1% w/v.

The following non-limiting Examples illustrate the preparation of compounds and compositions of the present invention. All temperatures are in °C.

EXAMPLE 1

9-[(1,3-Dihydroxy-2-propoxy)methyl]guanine cyclic pyrophosphate

A. Freshly distilled $POCl_3$ (2.5 ml) and $(EtO)_3PO$ (14.4 ml) were mixed and cooled in an ice-bath. To this stirred solution was added 9-[(1,3-dihydroxy-2-propoxy)methyl]guanine dihydrate (1.01 g, 3.47 mmol) which may be prepared as disclosed in U.S. Pat. No. 4,355,032, and the mixture was stirred at 0° for 20 hours. The reaction mixture was then added dropwise to anhydrous ethyl ether (350 ml) and petroleum ether (100 ml) was added. The white precipitate so formed was filtered off and dissolved in 0.1M $NH_4OH$ (100 ml) and the solution was evaporated to dryness. This residue was dissolved in a little water and applied to a Dowex 1 × 2 ($HCOO^-$) column (3.0 × 32.0 cm). The column was developed with water (315 ml), followed by a linear gradient of water (2 liters) to 5N HCOOH (2 liters), and then with 1M $HCOONH_4$ (500 ml) and finally, 2M $HCOONH_4$ (500 ml). Fractions containing the bis-monophosphate (2.185 mmol, by uv estimate, 73.4%) were pooled and evaporated to dryness. The residue was boiled with methanol (200 ml) and then filtered while hot. The solid was washed on the pad with hot methanol and then ethyl ether to give 804 mg of analytically pure material as the diammonium salt, dihydrate of 9-[(1,3-dihydroxy-2-propoxy)methyl]guanine bis-monophosphate (Compound 1A). A second crop from the filtrate gave an additional 162 mg.

Anal. Calculated for $C_9H_{21}N_7P_2O_{10}.2H_2O$: C, 23.14; H, 4.95; N, 20.99, P, 13.26. Found: C, 23.29; H, 4.63; N, 20.79; P, 13.24.

UV (0.01N NaOH): $\lambda max$ 261 (11,510), $\lambda min$ 231 (5,340) (0.01N HCl): $\lambda max$ 255 (12,460, sh272 (8,620), $\lambda min$ 227 (3,530).

The product had the expected retention time on high pressure liquid chromatography and NMR (200 $MH_z$, $D_2O$) was consistent with the proposed structure. Treatment of a small portion of the product with bacterial alkaline phosphate gave the 9-[(1,3-dihydroxy-2-propoxy)methyl]guanine.

B. Compound 1A (0.500 g; 1.07 mmol) was dissolved in water (21 ml) and pyridine was added until the solution was just opalescent (188 ml of pyridine). Dicyclohexylcarbodiimide was then added to the well-stirred solution in 2.0–2.5 g aliquots at approximately 24 hour intervals until 16.0 g had been added (7 days total). Water (30 ml) was added and the reaction left overnight. The mixture was evaporated to dryness and the residue was separated between water (200 ml) and ethyl ether (200 ml). The solid material was filtered off and the layers were separated. Ammonium hydroxide (1 ml) was added to the aqueous layer which was then evaporated to dryness. The residue was dissolved in a little water and applied to a DEAE-Sephadex column (3.0 × 26.0 cm, in the $HCO_3^-$ form). The column was developed successively with water (500 ml), 0.1M $NH_4HCO_3$ (500 ml) and then with a linear gradient of 0.1M $NH_4HCO_3$ (2 liters) to 0.4M $NH_4HCO_3$ (2 liters). Fractions containing the required product, the title compound, were pooled and evaporated to dryness (0.854 mmol by uv estimate, 79.8%). Analytical data was obtained on a lyophilized sample.

Calculated for $C_9H_{13}N_5O_9P_2.1.75NH_3.2H_2O$: C, 23.35; H, 4.82; N, 20.42. Found: C, 23.13; H, 4.37; N, 20.40.

The disodium salt could be prepared from the foregoing using a CM-52 ($Na^+$ form) carboxymethyl cellulose column. Analytically pure material could be obtained by crystallization from isopropanol-water.

Calculated for $C_9H_{11}N_5O_9P_2Na_2.3.5H_2O$: C, 21.44; H, 3.60; N, 13.89. Found: C, 21.47; H, 3.19; N, 13.61.

uv (pH 7.5, phosphate buffer) $\lambda max$ 252 (15,740), shoulder 270 (11,490), (0.01M HCl), $\lambda max$ 255 (12,760), shoulder 270 (9,360), (0.01M NaOH), $\lambda max$ 260 (11,910).

The product had the expected retention time on high pressure liquid chromatography and NMR (200 $MH_z$, $D_2O$) was consistent with the proposed structure. Enzymatic degradation with pyrophosphatase gave 9-[(1,3-dihydroxy-2-propoxy)methyl]guanine bis-monophosphate.

EXAMPLE 2

9[(1,3-Dihydroxy-2-propoxy)methyl]adenine cyclic pyrophosphate

A. Freshly distilled $POCl_3$ (0.3 ml) and $EtO)_3PO$ (1.7 ml) were mixed and stirred in an ice-bath for 15 minutes. 9-[(1,3-dihydroxy-2-propoxy)methyl]adenine (100 mg, 0.42 mmol), which may be prepared as disclosd in U.S. Pat. No. 4,347,360, was added and the solution was stirred for 22 hours at 0°–4° C. The reaction mixture was poured into $Et_2O$ (50 ml)-petroleum ether (50 ml) and the solution was extracted with 0.1M $NH_4OH$ (4 × 50 ml). 1M $NH_4OH$ (1 ml) was added to the pooled aqueous layers and which was then evaporated to dryness. The residue was dissolved in a little water and applied to a Dowex 1 × 2 ($HCOO^-$ form) column (2.0 × 16.0 cm). After developing with water (600 ml), a linear gradient of water (1500 ml) to 1.75M $HCOONH_4$ (1500 ml) was commenced. Two major peaks were eluted, the first was the enantiomeric monophosphate mixture 9-[(1,3-dihydroxy-2-propoxy)methyl]adenine monophosphate (yield, 0.126 mmol, 30%) and then fractions containing the required product (yield 0.144 mmol, 34%) were pooled and evaporated to dryness. The residue was triturated with ethanol and the product was filtered off as the diammonium salt of 9-[(1,3-dihydroxy-2-propoxy)methyl]adenine bis-monophosphate (Compound 2A) (44 mg).

Anal. Calculated for $C_9H_{21}N_7O_9P_2.H_2O$: C, 23.95; H, 5.13; N, 21.73. Found: C, 24.29; H, 4.88; N, 21.30.

uv (pH 7.5, 0.05M $K_2HPO_4$—$KH_2PO_4$) $\lambda max$ 260 (15,210).

The product had the expected retention time on high pressure liquid chromatography and NMR (200 mHz, D₂O) was consistent with the assigned structure.

Enzymatic degradation with bacterial alkaline phosphatase gave the 9-[(1,3-dihydroxy-2-propoxy)methyl]adenine.

B. Compound 2A (36 mg, 0.08 mmol) was dissolved in water (2 ml) and pyridine was added until the solution was just opalescent (20 ml of pyridine). Dicyclohexylcarbodiimide (1.0 g, in total) was then added to the well stirred solution in aliquots over a period of 10 days. An additional 2 ml of water was then added and the solution stirred overnight. The reaction was evaporated to dryness and to the residue was added ethyl ether (50 ml) and water (50 ml). The insoluble material was filtered off and the layers were separated. The aqueous layer was evaporated to dryness after the addition of a few drops of concentrated ammonium hydroxide. This residue was dissolved in a little water and applied to a DEAE-Sephadex (HCO₃⁻ form) column (2.0×15.0 cm). The column was developed first with water (500 ml) and then with a linear gradient of water (1.5 liters) to 0.4M NH₄HCO₃ (1.5 liters). Fractions containing the required product, the title compound, were pooled and evaporated to dryness. Yield 0.027 mmol, 34%. Repeated evaporation from water removed NH₄HCO₃ and lyophilization gave a white powder.

The product had the expected retention time on high pressure liquid chromatography and enzymatic degradation with pyrophosphatase gave 9-[(1,3-dihydroxy-2-propoxy)methyl[adenine bis-monophosphate. Bacterial alkaline phosphatase did not degrade the product under normal conditions.

EXAMPLE 3

1-[(1,3-Dihydroxy-2-propoxy)methyl]uracil cyclic pyrophosphate

A. Bis-2,4-trimethylsilyloxypyrimidine [3.51 g. 0.0137 mole (see T. Nishimura and I. Iwai, *Chem. Pharm. Bull.* (Tokyo) 12, 352 (1964)] and (1,3-diacetoxy-2-propyl) chloromethyl ether (3.08 g, 0.0137 moles) were combined and heated under house vacuum at 110° for 3 hours. After cooling to ambient temperature, 20 ml of methanol and 1 ml of water were added and the mixture was heated to reflux temperature for 30 minutes. The mixture was concentrated under reduced pressure and purified by flash chromatography on silica gel (40 mm column). The eluting solvent was 95 parts methylene chloride and 5 parts methanol (by volume). 1.9 g was obtained after concentration of fractions.

The acetylated uracil acyclonucleoside (1.8 g, 0.006 m) was heated in 20 ml of 40% aqueous methylamine for one hour at reflux temperature. The reaction mixture was filtered, concentrated under reduced pressure, and the crude product recrystallized from isopropanol. After filtration and drying 1.1 g of product was obtained, m.p. 123–124.

B. Freshly distilled POCl₃ (0.6 ml) and (EtO)₃PO (3.4 ml) were mixed and stirred at 0°–5° C. (ice-bath) for 15 minutes. Compound 2A (200 mg, 0.92 mmol) was added and the solution was stirred for 22 hours at 0°–4° C. The reaction mixture was poured into Et₂O (100 ml)-petroleum ether (100 ml) and the solution was extracted with 0.1M NH₄OH. Additional NH₄OH was added until the aqueous phase was neutral (about 1 ml). The aqueous phase was evaporated to dryness and the residue was dissolved in a little H₂O and applied to a Dowex 1×2 (HCOO⁻ form) column (3.0×16.0 cm). After developing first with water, a linear gradient of water (1500 ml) to 2M HCOONH₄ (1500 ml) was commenced. Fractions containing the required product (0.8 mmol, 87%) were pooled and evaporated to dryness. The residue was triturated with EtOH (2×150 ml) and the precipitate was filtered off and dried. The yield was 342 mg. This chromatographically pure product (Compound 3B) had the expected retention time on high pressure liquid chromatography and was used directly in the next step.

C. Compound 3B (0.7 mmol) was dissolved in water (15 ml) and pyridine was added until the solution became opalescent (150 ml of pyridine). Dicyclohexylcarbodiimide (1.0 g) was added and the solution was stirred. Additional aliquots of dicyclohexylcarbodiimide were added every 24 hours until 4.0 g in total had been added. High pressure liquid chromatography after 4 days showed complete reaction and the mixture was evaporated to dryness. The residue was treated with Et₂O (150 ml)-water (150 ml) and the solid was filtered off. The layers were separated and 1 ml of NH₄OH was added to the aqueous layer prior to evaporation to dryness. The residue was dissolved in a little water and applied to a DEAE Sephadex column (HCO₃⁻ form; 3×21 cm). After developing with water (500 ml) a linear gradient of water (1500 ml) to 0.4M NH₄HCO₃ (1500 ml) was commenced. Fractions containing the required product (0.19 mmol, 27%) were pooled and evaporated several times to dryness in vacuo (this also removed the NH₄HCO₃). Lyophilization gave a white powder (78 mg). This product had the expected retention time on high pressure liquid chromatography and enzymatic degradation with pyrophosphatase gave 1-[(1,3-dihydroxy-2-propoxy)methyl]uracil bis-monophosphate.

EXAMPLE 4

9-[(2,3-Dihydroxy-1-propoxy)methyl]guanine cyclic monophosphate

Freshly distilled POCl₃ (0.9 ml) and (EtO)₃PO (5.1 ml) were mixed and stirred in an ice bath for 15 minutes. 9-[(2,3-Dihydroxy-1-propoxy)methyl]guanine (300 mg, 1.18 mmol) was then added and the suspension was stirred at 0°–5° C. overnight. At this time, total solubility was apparent and the reaction mixture was poured into Et₂O (150 ml)-petroleum ether (150 ml). The white precipitate so formed was filtered off and washed with Et₂O: petroleum ether (1:1, 20 ml). This material was dissolved in water and the solution was neutralized with dilute NH₄OH, before being evaporated to dryness. The residue was dissolved in a little water and applied to a Dowex 1×2 (HCOO⁻ form) column (3×18 cm). After developing with water (500 ml), a linear gradient of water (1500 ml) to 2M HCOONH₄ (1500 ml) was commenced. Fractions containing the required product (0.77 mmol, 65%) were pooled and evaporated to dryness. The residue was triturated under EtOH to remove HCOONH₄ (checked by NMR) and the white solid was filtered off and dried in vacuo.

The product had the expected retention time on high pressure liquid chromatography and was not degraded with bacterial alkaline phosphatase.

EXAMPLE 5

9-[(2,3-Dihydroxy-1-propoxy)methyl]guanine cyclic pyrophosphate

A. 9-[(2,3-Dihydroxy-1-propoxy)methyl]guanine is phosphorylated with bis(2,2,2-trichloroethyl)phosphorochloridate or bisbenzylphosphorochloridate in pyridine or triethyl phosphate to give the protected bismonophosphate. Deblocking by standard methods gives 9-[(2,3-dihydroxy-1-propoxy)methyl]guanine 2',3'-bismonophosphate (compound 5A) which is purified by anion exchange chromatography in the usual fashion.

B. Compound 5A is dissolved in water and pyridine is added until the solution becomes just opalescent. Dicyclohexylcarbodiimide is then added every 24 hours until high pressure liquid chromatography indicates complete conversion to the cyclic pyrophosphate. The reaction mixture is evaporated to dryness and the residue triturated under Et₂O-water (1:1, by volume). The insoluble material (dicyclohexylurea) is filtered off and the layers in the filtrate are separated. The aqueous layer is evaporated to dryness and the residue dissolved in a little water and fractionated by anion exchange chromatography to give the title compound.

EXAMPLE 6

Oil in Water Cream Base

| | |
|---|---|
| 9-[(1,3-dihydroxy-2-propoxy)methyl]guanine 1',3'-cyclic-pyrophosphate | 5.0 g |
| Lanolin, Anhydrous | 20.0 g |
| Polysorbate 60 | 4.0 g |
| Sorbitan Monopalmitate | 2.0 g |
| Light Liquid Paraffin | 4.0 g |
| Propylene Glycol | 5.0 g |
| Methyl Hydroxylbenzoate | 0.1 g |
| Purified Water | to 100.0 g |

EXAMPLE 7

Water Soluble Ointment Base

| | |
|---|---|
| 9-[(1,3-dihydroxy-2-propoxy)methyl]guanine 1',3'-cyclic-pyrophosphate | 0.5 g |
| Glycerol | 15.0 g |
| Macrogol 300 | 20.0 g |
| Polyethylene Glycol 1500 | 64.5 g |

EXAMPLE 8

Tablet—(Total weight 359 mg)

| | |
|---|---|
| 9-[(1,3-dihydroxy-2-propoxy)methyl]guanine 1',3'-cyclic-pyrophosphate | 100 mg |
| Lactone | 200 mg |
| Starch | 50 mg |
| Polyvinylpyrrolidone | 5 mg |
| Magnesium Stearate | 4 mg |

EXAMPLE 9

Tablet—(Total weight 359 mg)

| | |
|---|---|
| 9-[(1,3-dihydroxy-2-propoxy)methyl]adenine 1',3'-cyclic-pyrophosphate | 100 mg |
| Lactone | 200 mg |
| Starch | 50 mg |
| Polyvinylpyrrolidone | 5 mg |
| Magnesium Stearate | 4 mg |

Combine the ingredients for each of the formulations of Examples 6 through 9 by standard techniques. Substitute other compounds of the present invention in these formulations to prepare other pharmaceutical compositions.

What is claimed is:

1. A compound of the formula R—CH₂—O—W and its pharmaceutically acceptable salts wherein R is a purine, a substituted purine, a pyrimidine or a substituted pyrimidine, wherein the substituents on the purine or pyrimidine are selected from amino, hydroxyl, halogen, thiol or alkylthiol wherein the alkyl moiety of the alkylthiol has 1 to 6 carbon atoms; and W is

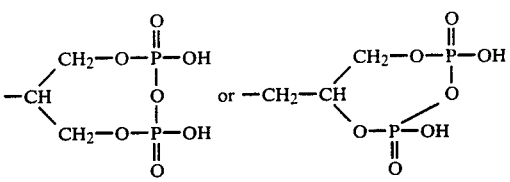

2. A compound according to claim 1, wherein W is

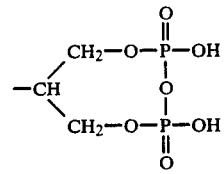

3. A compound according to claim 1, wherein W is

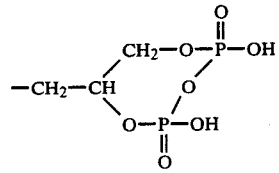

4. A compound according to claim 1, wherein the purine or substituted purine is attached at its 9-position and the pyrimidine or substituted pyrimidine is attached at its 1-position.

5. A compound according to claim 1, wherein the substituted purine, is a mono- or disubstituted purine and the substituted pyrimidine is a di- or trisubstituted pyrimidine.

6. A compound according to claim 1, wherein R is guanine, adenine, 2,6-diaminopurine, cytosine, thymine, uracil or 5-fluorouracil.

7. A compound according to claim 2, wherein R is guanine, adenine, 2,6-diaminopurine, cytosine, thymine, uracil or 5-fluorouracil.

8. A compound according to claim 3, wherein R is guanine, adenine, 2,6-diaminopurine, cytosine, thymine, uracil or 5-fluorouracil.

9. 9-[(1,3-Dihydroxy-2-propoxy)methyl]guanine cyclic pyrophosphate, according to claim 1.

10. 9-[(1,3-Dihydroxy-2-propoxy)methyl]adenine cyclic pyrophosphate, according to claim 1.

11. 1-[1,3-Dihydroxy-2-propoxymethyl]uracil cyclic pyrophosphate, according to claim 1.

12. 9-[(2,3-Dihydroxy-1-propoxy)methyl]guanine cyclic pyrophosphate according to claim 1.

13. A anti-viral pharmaceutical composition comprising an effective amount of a compound of claim 1 and a pharmaceutically acceptable carrier.

14. A method of treating herpes type virus infection in mammals comprising administering to a patient in need of such treatment an effective amount of a compound of claim 1.

* * * * *